(12) United States Patent
Franklin

(10) Patent No.: US 7,276,050 B2
(45) Date of Patent: Oct. 2, 2007

(54) TRANS-SCLERAL DRUG DELIVERY METHOD AND APPARATUS

(76) Inventor: Alan Franklin, 325 Magnolia Vale Dr., Chattanooga, TN (US) 37419

( * ) Notice: Subject to any disclaimer, the term of this patent is extended or adjusted under 35 U.S.C. 154(b) by 274 days.

(21) Appl. No.: 10/791,487

(22) Filed: Mar. 2, 2004

(65) Prior Publication Data

US 2005/0197637 A1    Sep. 8, 2005

(51) Int. Cl.
*A61M 35/00* (2006.01)
(52) U.S. Cl. .................. 604/294; 604/521; 424/427
(58) Field of Classification Search ............. 604/289, 604/521, 294, 890.1, 891.1, 93.01; 424/423, 424/424, 427, 428
See application file for complete search history.

(56) References Cited

U.S. PATENT DOCUMENTS

| | | |
|---|---|---|
| 4,590,201 A | 5/1986 | Bochis et al. |
| 5,098,443 A | 3/1992 | Parel et al. |
| 5,132,315 A | 7/1992 | Kohn et al. |
| 5,177,074 A | 1/1993 | Allen et al. |
| 5,177,095 A | 1/1993 | Greenlee et al. |
| 5,187,179 A | 2/1993 | Ashton et al. |
| 5,234,917 A | 8/1993 | Finkelstein et al. |
| 5,300,114 A | 4/1994 | Gwon et al. |
| 5,488,050 A | 1/1996 | Neufeld |
| 5,602,156 A | 2/1997 | Kohn et al. |
| 5,744,492 A | 4/1998 | Kohn et al. |
| 6,126,687 A | 10/2000 | Peyman |
| 6,239,137 B1 | 5/2001 | Karmali et al. |
| 6,413,540 B1 | 7/2002 | Yaacobi |
| 6,416,777 B1 * | 7/2002 | Yaacobi ............... 424/428 |
| 6,420,399 B1 | 7/2002 | Graff et al. |
| 6,599,910 B1 | 7/2003 | Adams et al. |
| 2002/0010176 A1 | 1/2002 | Askew et al. |
| 2002/0086862 A1 | 7/2002 | Baxter et al. |
| 2002/0183365 A1 | 12/2002 | Wagle et al. |
| 2002/0188282 A1 | 12/2002 | Greenberg |
| 2003/0013712 A1 | 1/2003 | Tullis et al. |
| 2003/0014036 A1 | 1/2003 | Varner et al. |
| 2003/0100558 A1 | 5/2003 | Tullis et al. |
| 2003/0114416 A1 | 6/2003 | Pulaski et al. |
| 2003/0125361 A1 | 7/2003 | Clare et al. |
| 2003/0143199 A1 | 7/2003 | Carson et al. |
| 2003/0149051 A1 | 8/2003 | Green et al. |
| 2004/0198829 A1 * | 10/2004 | Sponsel et al. ............. 514/573 |
| 2005/0113806 A1 * | 5/2005 | De Carvalho et al. ... 604/890.1 |

FOREIGN PATENT DOCUMENTS

JP         2275866         11/1990

* cited by examiner

Primary Examiner—Kevin C. Sirmons
Assistant Examiner—Catherine N. Witczak
(74) Attorney, Agent, or Firm—Husch & Eppenberger LLC; H. Frederick Rusche

(57) ABSTRACT

A method of treating ocular disorders involving angiogenesis includes the steps of providing a trans-scleral drug delivery device comprising an insert stabilizer for attachment to a scleral surface and having an interlock opening and a replaceable implant having a reservoir adjacent the scleral surface and an interlock tab, wherein said insert stabilizer and said replaceable implant are removeably connectable by mating said interlock tab and said interlock opening; providing an anti-angiogenic factor; introducing said anti-angiogenic factor into said reservoir; and attaching said insert stabilizer to the scleral surface. The reservoir can be refilled by disengaging the implant from the stabilizer, inserting a new dosage of anti-angiogenic factor, and reconnecting the implant to the stabilizer or injecting a new dosage of anti-angiogenic factor into the reservoir through an injection port in the stabilizer.

3 Claims, 7 Drawing Sheets

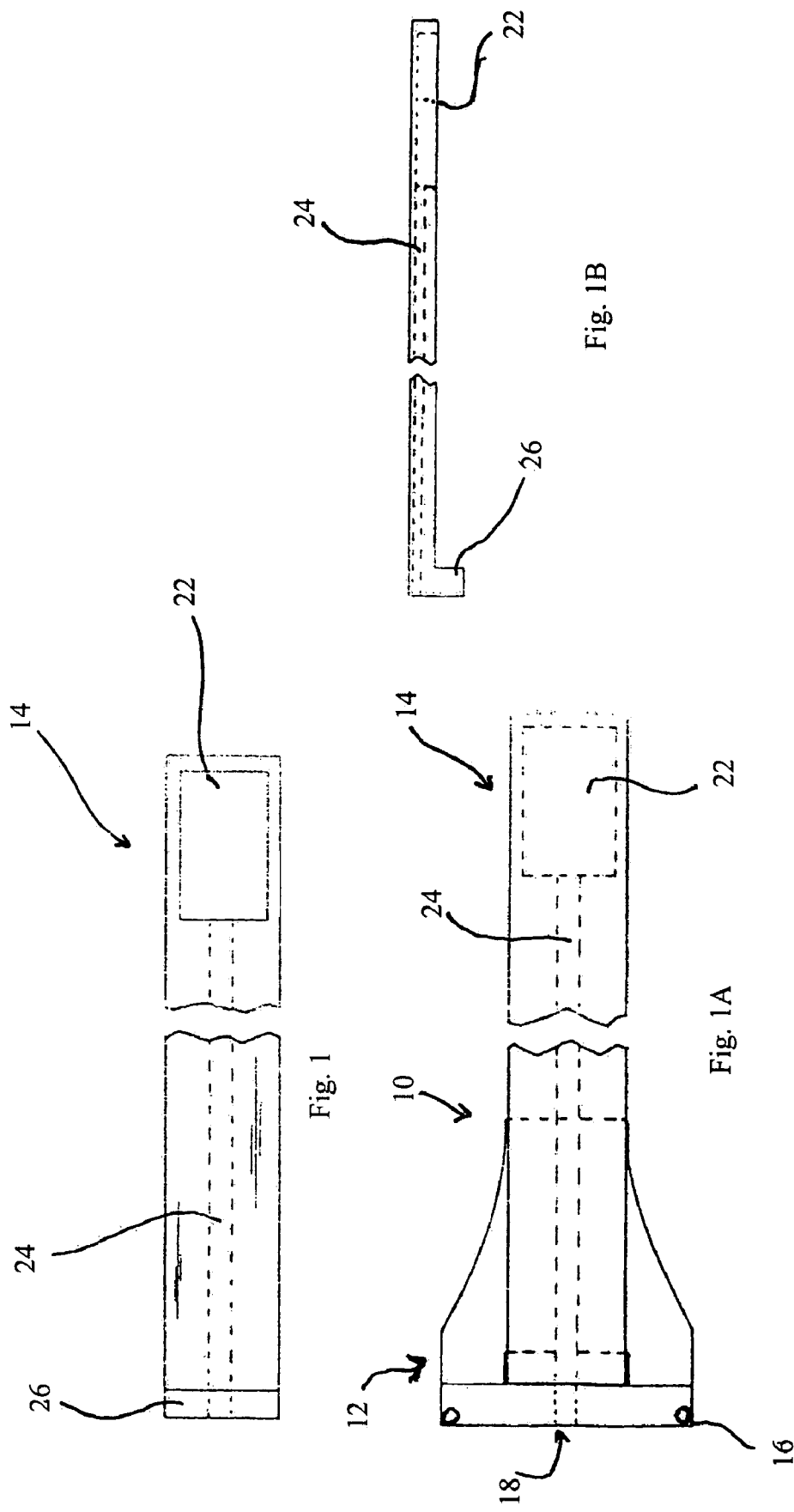

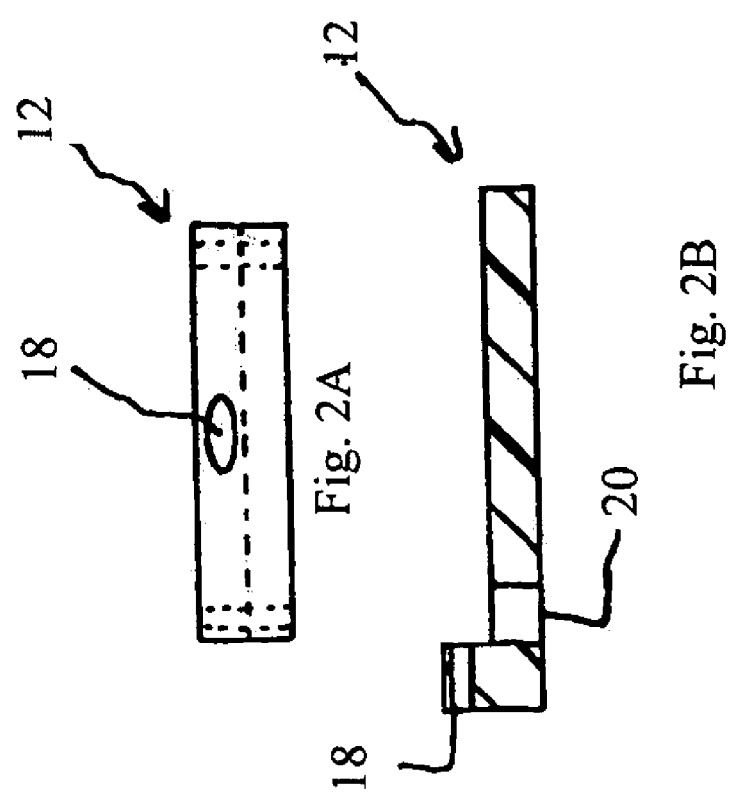
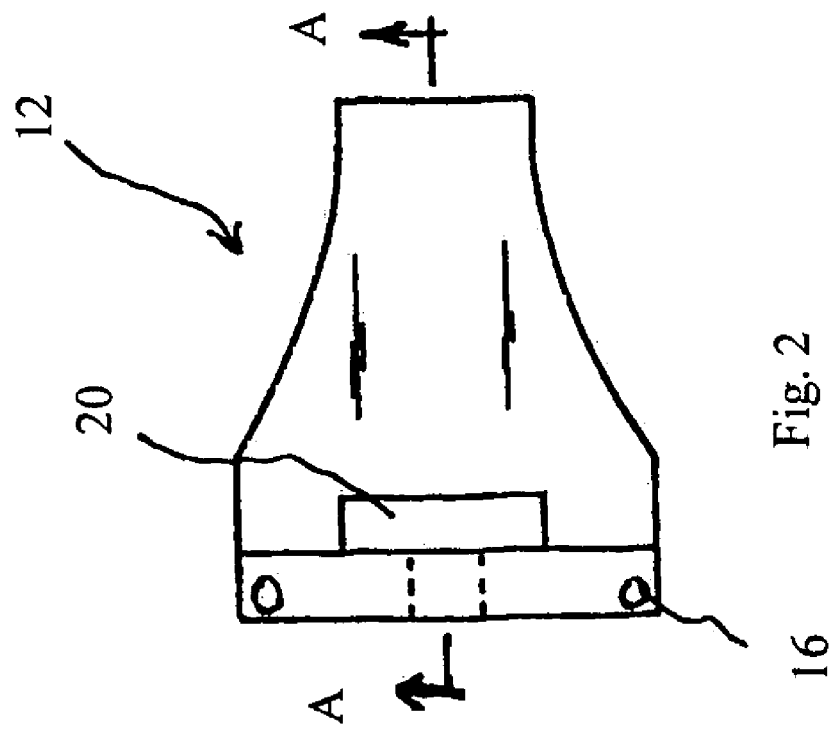

TRANS-SCLERAL DRUG DELIVERY METHOD AND APPARATUS

TECHNICAL FIELD OF THE INVENTION

This invention generally relates to the treatment of ophthalmic conditions with localized delivery of pharmaceutically active agents and, more particularly, to a method of localized delivery of specific pharmaceutically active agents by means of a refillable trans-scleral delivery device.

DESCRIPTION OF THE RELATED ART

Age-related macular degeneration (AMD), diabetic retinopathy (DR), and retinal vein occlusions (RVO) are among a number of diseases where ocular neovascularization threatens vision. In particular, AMD and DR are two of the most common causes of legal blindness in the United States and Europe, and approximately a third of individuals over the age of seventy are afflicted with AMD. Choroidal neovascularization is found in 10-15% of individuals with AMD, but is responsible for 85% of cases with severe vision loss. Diabetic retinopathy, and, in particular, the pathological neovascularization associated therewith, is the leading cause of severe vision loss in adults between the ages of 28 and 64 in the United States and Europe.

Current approved treatment of both diabetic retinopathy (DR) and age-related macular degeneration (AMD) relies on either threshold or subthreshold laser energy. Threshold laser is inherently destructive and usually causes paracentral and central scotomata in patients with AMD, and limits peripheral and central vision in patients with diabetic retinopathy. Ocular photodynamic therapy (OPT) is approved for the treatment of predominantly classic choroidal neovascularization (CNVM) underneath the foveal center, but has not been approved by the FDA to treat occult subfoveal CNVM, the most common type of subfoveal neovascularization. Although OPT is an effective treatment for classic subfoveal CNVM, the results are far from ideal in that most patients require 3 or more sessions of OPT to eradicate the CNVM, and it only reduces the incidence of severe vision loss 3 lines by 15% over a 1 year time period. In addition, there is only a 5.0% incidence of a 2 line or greater vision improvement over this time compared to 2.4% observed with the natural history of the disease. Many groups have studied other modalities that include transpupillary thermoplasty (TTT), radiation, and foveal translocation to treat subfoveal CNVM, but most results demonstrate similar limited or less efficacy compared to OPT.

There are 4 anti-angiogenic molecules that are either involved in Phase II clinical trials that have completed enrolling patients or are under investigation in Phase III trials. Early data from Phase I and II trials demonstrate an approximate 25% incidence of 2 line or greater visual improvement observed after treatment of subfoveal CNVM with at least 3 out of 4 of these molecules, which is clearly superior to the current laser treatment modalities. The first of these molecules are protein kinase C inhibitors. These molecules target a retinal enriched enzyme and are orally administered. The second and third molecules bind with high affinity to VEGF, thereby blocking the action of this potent angiogenic growth factor. One mechanism of VEGF binding utilizes a modified oligonucleotide, aptamer (Macugen), while the other uses a fragment of a high affinity antibody. Both currently are administered by intravitreal injections at a frequency in the range of every 6 weeks. Finally, anecortave acetate is an anti-angiogenic steroid derivative, that is administered every six months by juxtascleral injection. The oral protein kinase C inhibitors have been used predominantly in the treatment of DR, while the aptamer, blocking antibody (RhuFab), and anecortave acetate are under testing to treat subfoveal CNVM in AMD. Only, one of these molecules relies upon trans-scleral delivery: anecortave acetate. The molecular weights of the other molecules are significantly higher (Macugen=10,000; RhuFab=48,000) so that their predicted range of trans-scleral permeability are orders of magnitude lower.

Effective treatment of neovascularization associated with AMD, DR, and RVO and other similar diseases with anti-angiogenic factors involves delivery of the factors to the posterior segment of the eye. However, the angiogenic process is desirable in other organs. Therefore, one challenge in the treatment of these diseases is the effective delivery of anti-angiogenic factors to the posterior segment of the eye without interfering with angiogenesis in other organ systems where it is beneficial.

Drug delivery to the posterior segment of the eye can be accomplished by four different methods: 1) systemic delivery, 2) topical drops, 3) intraocular or intravitreal delivery, and 4) trans-scleral delivery such as periocular injection or implants. The intravitreal half-life of a compound and the specific neovascular process to be treated are major determinants for the required frequency and/or duration of intravitreal injections. Topical administration to the ocular surface often does not influence posterior segment disease. Multiple intravitreal injections can cause scleral necrosis, and are difficult to tolerate. However, intravitreal sustained release devices for many agents deliver a prolonged and acceptable drug concentration to the posterior segment of the eye. If the sclera is relatively permeable to a drug, then multiple schemes can be developed to deliver a prolonged bioeffective concentration of that agent to the posterior segment, while avoiding potential complications of intraocular surgery such as cataract formation, glaucoma, retinal detachment, and endophthalmitis.

The present invention is directed to overcoming one or more of the problems set forth above.

SUMMARY OF THE INVENTION

An aspect of the present invention is to provide an improved and effective method for treating ocular disorders that involve angiogenesis to result in better visual acuity and fewer side effects.

Another aspect of the present invention is to provide an improved method of trans-scleral administration of anti-angiogenic factors.

Yet another aspect of the present invention is to provide a more efficient and less invasive means of filling and refilling a trans-scleral delivery device.

In accordance with the above aspect of the invention, there is provided a method of treating ocular disorders involving angiogenesis that includes the steps of providing a trans-scleral drug delivery device comprising an insert stabilizer for attachment to a scleral surface and having an interlock opening and a replaceable implant having a reservoir adjacent the scleral surface and an interlock tab, wherein said insert stabilizer and said replaceable implant are removeably connectable by mating said interlock tab and said interlock opening; providing an anti-angiogenic factor or combinations of anti-angiogenic factors; introducing said anti-angiogenic factor(s) into said reservoir; and attaching said insert stabilizer to the scleral surface. In accordance with another aspect of the invention, the method of treating ocular disorders includes refilling said trans-scleral drug delivery device by disengaging said replaceable implant from said insert stabilizer while leaving said insert stabilizer attached to the scleral surface, introducing a new dosage of anti-angiogenic factor(s) in said reservoir, and reconnecting said replaceable implant with said insert stabilizer.

These aspects are merely illustrative of the innumerable aspects associated with the present invention and should not be deemed as limiting in any manner. These and other aspects, features and advantages of the present invention will become apparent from the following detailed description when taken in conjunction with the referenced drawings.

BRIEF DESCRIPTION OF THE DRAWINGS

Reference is now made more particularly to the drawings, which illustrate the best presently known mode of carrying out the invention and wherein similar reference characters indicate the same parts throughout the views.

FIG. 1 is a schematic view of a trans-scleral drug delivery device according to one embodiment of the present invention.

FIG. 1A is a top view of a replaceable implant for a trans-scleral drug delivery device.

FIG. 1B is a side view of the replaceable implant of FIG. 1A.

FIG. 2 is a schematic view of an insert stabilizer for a trans-scleral drug delivery device according to one embodiment of the present invention.

FIG. 2A is an end view of the insert stabilizer of FIG. 2.

FIG. 2B is a section view of the insert stabilizer of FIG. 2 taken along line A-A.

DETAILED DESCRIPTION

Figures 3A, 3B:
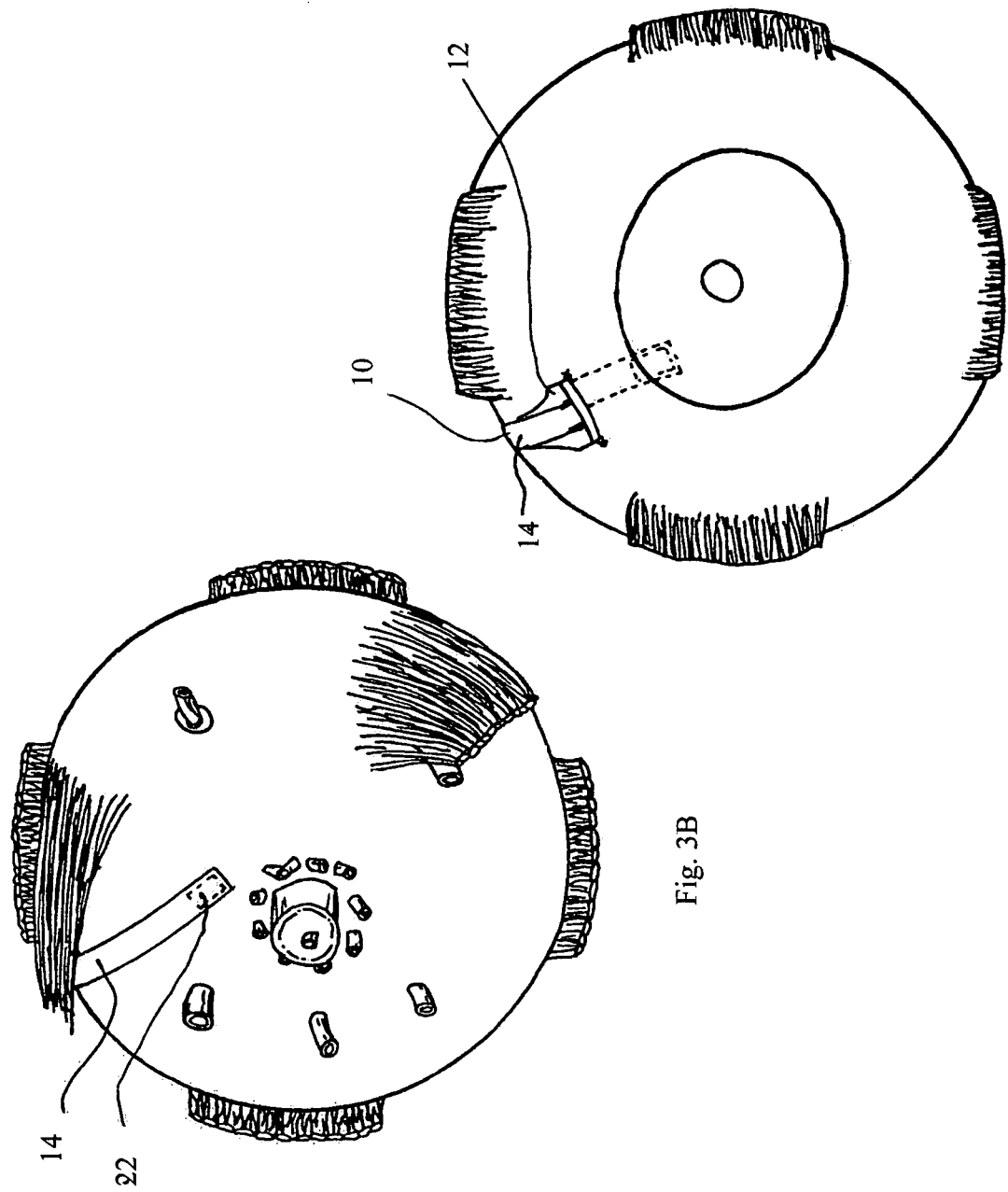
FIG. 3A is a schematic view illustrating a trans-scleral drug delivery device as positioned on an eye.
FIG. 3B is a view of the trans-scleral drug delivery device of FIG. 3A from the rear.

In the following detailed description numerous specific details are set forth in order to provide a thorough understanding of the invention. However, it will be understood by those skilled in the art that the present invention may be practiced without these specific details. For example, the invention is not limited in scope to the particular type of industry application depicted in the figures. In other instances, well-known methods, procedures, and components have not been described in detail so as not to obscure the present invention.

An ideal candidate molecule for the treatment of retinal and/or choroidal neovascularization should (1) be relatively non-toxic, (2) have reasonable bioavailability in ocular tissues, (3) have some physiologic basis to be studied, and (4) not adversely interfere with other physiological neovascular responses such as would healing nad coronary vascular remodeling. Carboxyamido-triazole (CAI) is an anti-angiogenic factor that has shown considerable promise in view of these requirements.

CAI is an anti-angiogenic factor that is undergoing clinical trials for the treatment of different human cancers. CAI, originally developed as a coccidiostat, was subsequently shown to have potent antiproliferative and antimetastatic effects in many animal models. U.S. Pat. No. 4,590,201 discusses the structure and anticoccidial activity of CAI. U.S. Pat. No. 5,132,315 discusses the use of CAI in the treatment certain human cancers. Finally, U.S. Pat. No. 5,744,492 discusses the anti-angiogenic activity of CAI. U.S. Pat. Nos. 4,590,201; 5,312,315; and 5,744,492 are hereby incorporated by reference.

CAI decreases intracellular calcium by inhibition of non-voltage gated calcium channels, the predominant calcium channel type present on endothelial cells. This reduction of intracellular calcium diminishes endothelial cell proliferation and division. In addition, CAI antagonizes expression of many pro-angiogenic cytokines that include VEGF as well as their downstream intracellular effects. Furthermore, CAI inhibits the growth and metastasis of many tumors that are associated with local tumor ischemia, increased VEGF expression, and pathological angiogenesis. These data suggest that CAI may be a candidate as an inhibitor of pathological ocular neovascularization.

Testing of CAI in a mouse pup model of hyperoxia-induced ocular neovascularization, in which posterior retinal ischemia mediates of pathological angiogenesis, has confirmed that CAI is a potent inhibitor of ocular angiogenesis in this model. CAI nearly completely abolished formation of neovascular fronds, and caused a dramatic and significant regression of preformed neovascular fronds. Immunohistochemistry and light microscopy studies established that this event was associated with up regulation of intracellular bcl-2 and relative protection of normal cellular morphology in the ischemic inner plexiform layer.

Of particular interest is the fact that CAI may be administered by trans-scleral delivery. According to a preferred embodiment of the disclosed method, a trans-scleral implant is provided to administer a dosage of CAI. An embodiment of such an implant is illustrated in FIGS. 1 and 2. The implant 10 consists of two pieces: an insert stabilizer 12 and a replaceable insert 14. The stabilizer 12 is sutured to the sclera via a pair of eyelets 16 associated with the stabilizer 12. The stabilizer 12 includes an injection port 18 at the sutured end. The stabilizer 12 is arranged in a generally triangular shape, with the wide side of the triangle sutured to the eye, for increased stability of the implant 10. The stabilizer 12 has an interlock opening 20 to allow it to mate with the replaceable implant 14.

The replaceable implant 14 is provided with a generally elongated rectangular shape with a drug reservoir 22 at one end. The drug reservoir 22 is positioned in contact with the scleral surface when the stabilizer 12 and replaceable implant 14 are interlocked. The reservoir 22 is open and adjacent to the scleral surface, thereby promoting contact of the anti-angiogenic factor with the scleral surface and resulting in diffusion of the factor through the sclera. A tube 24 passing through the interior length of the implant 14 fluidly connects the reservoir 22 with the opposite end of the implant 14. The implant 14 is provided with an interlock tab 26 at the end opposite the reservoir 22. The interlock tab 26 mates with the interlock opening 20 of the stabilizer 12 to secure the two pieces together. When mated together, the interlock tab 26 and opening 20 are arranged to align the tube 24 of the implant 14 with the injection port 18 of the stabilizer, thereby fluidly connecting the drug reservoir 20 with the injection port 18. By this method, the anti-angiogenic agent can be placed into the whether it is in a fluid or solid formulation. Examples of a solid formulation may include a bioerodible implant formulated according to U.S. Pat. Nos. 4,882,150 and 4,865,846, and examples of a liquid formulation may include nanoparticle technology according to U.S. Pat. Nos. 6,632,671; 6,579,519; 6,506,411; and 6,506,411 or suspension such as used for triamcinalone for ocular administration. U.S. Pat. Nos. 4,882,150; 4,865,846; 6,632,671; 6,579,519; 6,506,411; and 6,506,411 are hereby incorporated by reference.

FIGS. 3A and 3B illustrated a preferred positioning of the trans-scleral implant 10 on the eye. Preferably, the anterior portion of the implant is approximately 2 mm anterior to the insertion of the lateral rectus muscle and centered in the quadrant between the lateral and superior recti muscles. The posterior portion of the implant terminates in a slightly temporal and superior position relative to the optic nerve.

The arrangement of the trans-scleral implant 10 provides a ready means for refill of the implant without the need to remove the entire implant and subsequently re-suture the implant to the scleral surface, thereby making refill more efficient and pleasant and less invasive for the patient. After initial insertion and suturing of the implant 10, it can be refilled by simply disconnecting the replaceable implant 14 from the stabilizer 12, refilling the reservoir 22 of the replaceable implant 14 or replacing the implant 14 with a new implant that is pre-filled, and reconnecting the replaceable implant 14 with the stabilizer 12 via the interlock combination 20, 26. Alternately, for liquid formulations of the anti-angiogenic agent, the port 18 may be re-injected. FIG. 2 illustrates one possible position for the implant 10 on a patient's sclera. However, it will be understood by those skilled in the art that proper positioning of the implant 10 will vary from patient to patient.

The implant 14 and stabilizer 12 are made of a hard silicone material in a preferred embodiment. Advantageously, the injection port 18 is provided with a non-silicone membrane to allow more efficient injection of liquid formulations or suspensions for the anti-angiogenic factor.

The anti-angiogenic factor(s) may be administered via the implant in either pellet form or as a liquid or suspension. When the anti-angiogenic factor is administered in pellet form, refilling of the implant 10 occurs as described above. When the anti-angiogenic factor(s) is provided in liquid or suspension form, refilling occurs in a different manner. In particular, the replaceable implant 14 is left in place and interlocked with the stabilizer 12. The anti-angiogenic factor (s) is injected through the injection port 18 in the stabilizer 12, which fluidly communicates with the drug reservoir 22. After injection of the anti-angiogenic factor, a fibrin sealant can also be injected through the injection port 18 to seal the port and prevent leakage of the anti-angiogenic factor.

While the trans-scleral delivery device described herein has been discussed in conjunction with the trans-scleral delivery of anti-angiogenic factors, it will be understood by those skilled in the art that the device is suitable for use for any number of pharmaceutical agents that may be administered by trans-scleral delivery.

The trans-scleral delivery of CAI will now be further illustrated with reference to the following non-limiting examples.

Biological Example

Scleral tissue was obtained from 23 human donor eyes (Georgia Eye Bank, Atlanta) and was stored in moist chambers for 2-6 days post-mortem. The mean age at time of death ($\pm$SE) for the donor tissue used in this study was 52.4$\pm$4.4 years. Scleral tissue was dissected from the superotemporal quadrant of each eye to minimize associated structures that can modify scleral permeability such as vortex veins, posterior ciliary arteries, and anterior ciliary vessels. Uveal tissue and episclera were carefully removed using a cotton-tip applicator. The sclera was mounted horizontally in a 2 chamber acrylic perfusion apparatus (FIG. 1). The uveal surface was apposed to the lower flow-through hemi-chamber (volume 500 µL) containing balanced salt solution (BSS, Alcon laboratories, Ft. Worth, Tex.). The test solution was applied to the episcleral surface. Since CAI has a 423 Da molecular weight and the molecule is hydrophobic with a solubility of 1-10 µM in water, three different test solutions that contained carboxyamido-triazole were evaluated: CAI in 20% DMSO (80% BSS vol/vol) at a concentration (mean$\pm$SE) of 15.2$\pm$3.0 µM (solution A), CAI in 10% DMSO (90% BSS) at a concentration of 4.1$\pm$0.4 µM (solution B), and CAI in 10% ethanol (90% BSS) at a concentration of 3.3$\pm$0.2 µM (solution C).

The BSS in the lower hemi-chamber was perfused at a rate of 0.03 ml/min. The perfusion apparatus was placed on a magnetic stir plate and mixing in the lower hemi-chamber was achieved using a stir bar. The upper hemi-chamber containing the test compound was covered with parafilm and sealed with silicone grease to prevent evaporation. This also provided a flexible seal so that trans-scleral pressure would not be altered. The temperature of the apparatus was maintained at 37° C. by a water jacket with circulating water bath.

A physiologic pressure of 15 mm Hg was applied across the sclera by raising the height of the outflow tube of the receptor (lower-) chamber to 22 cm. A pressure transducer that was connected to the lower hemi-chamber verified the pressure. For all three solutions that contained carboxyamido-triazole 100 µl was applied to the episcleral side and samples of perfusate were collected at the uveal side of the sclera at time zero and at 30-minute intervals for the duration of 8 hours. The scleral permeability to CAI in a 10% ethanol solution was also evaluated over a longer period of 24 hours of which samples were taken hourly. For the 24 hours experiments 500 µl of the test solution was added to the upper hemi-chamber to minimize depletion of the drug on the donor side.

From each sample obtained from the trans-scleral diffusion experiments an aliquot of 100 µl was taken and the concentrations of CAI were monitored by reverse-phase high-performance liquid chromatography (HPLC). Results were calculated on the basis of peak areas. Samples were analyzed by using a Hewlett Packard HP1100 HPLC system equipped with a UV detector, an auto-sampler, a pump, and a HP Kayak workstation that controls the operation of HPLC and analyzes the data. A Zorbak Rx-C8 column (4.6$\times$250 mm) was used for separation and detection was set at 260 nm. The flow rate employed was 1.0 ml/min with mobile phase of 55% acetonitrile and 45% water. The injection volume was 100 µl and retention time of CAI was about 7.8 minutes.

Steady state permeability constants were calculated from the data as:

$$K_{trans}=[R_{total}/(t)(A)]\times 1/[D]$$

Where $R_{total}$ is the amount of drug in the receiver effluent per collected fraction, and t is the fraction collection time (in seconds). A is the area of exposed sclera (in square centimeters). This value—$R_{total}/(t)(A)$—is equal to the flux across the tissue. D is the concentration of drug in the donor hemi-chamber. Permeability thus represents the steady state flux normalized by donor concentration. The area of exposed sclera was 0.385 cm2. Mean steady state permeability values (±SE) were calculated from four to eight experiments performed for each compound.

At the end of the trans-scleral diffusion experiments with CAI (DMSO 10%, 20%, and ethanol 10%) and 2ME2 (1% DMSO) the scleral tissue was fixed in 2.5% glutaraldehyde in 0.1 M sodium cacodylate buffer and prepared for transmission electron microscopy (TEM). The scleral tissue was bisected and postfixed in 2% osmium tetroxide for 2 hours. Small pieces of the sclera were embedded in low-viscosity epoxy medium, thin sectioned, stained with uranyl acetate and lead citrate, and viewed with a JEOL 100 CX transmission electron microscope. The micrographs were taken at X 2850.

Figure 4:
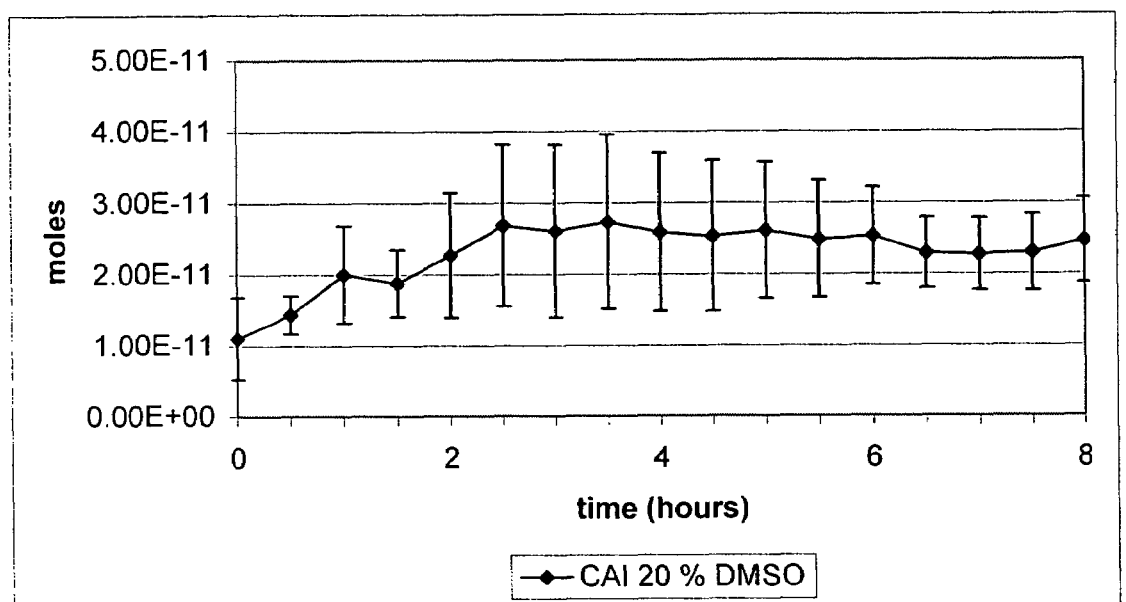
FIG. 4 is a chart illustrating the trans-scleral diffusion of a (mean±SE) 15.2±3.0 µM CAI solution in 20% DMSO (80% BSS vol/vol). Moles of CAI measured in the receiver chamber (n=4) as a function of time during BSS perfusion (0.03 ml/min) through the receiver (uveal) chamber. Each point represents the mean±SE.
Figure 5:
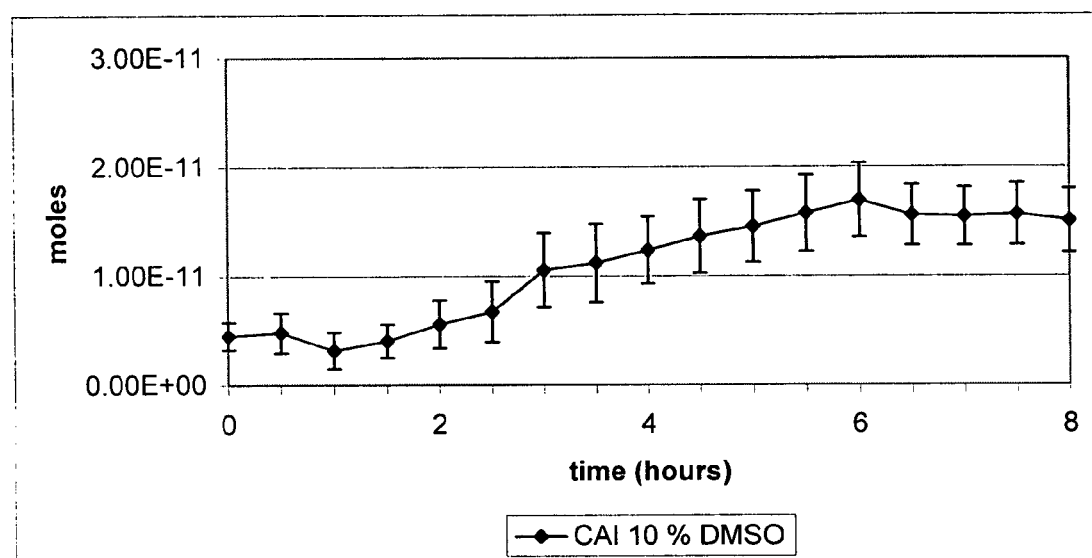
FIG. 5 is a chart illustrating the trans-scleral diffusion of a (mean±SE) 4.1±0.4 µM CAI solution in 10% DMSO (90% BSS). Moles of CAI measured in the receiver chamber (n=7) as a function of time during BSS perfusion (0.03 ml/min) through the receiver (uveal) chamber. Each point represents the mean±SE.
Figure 6A:
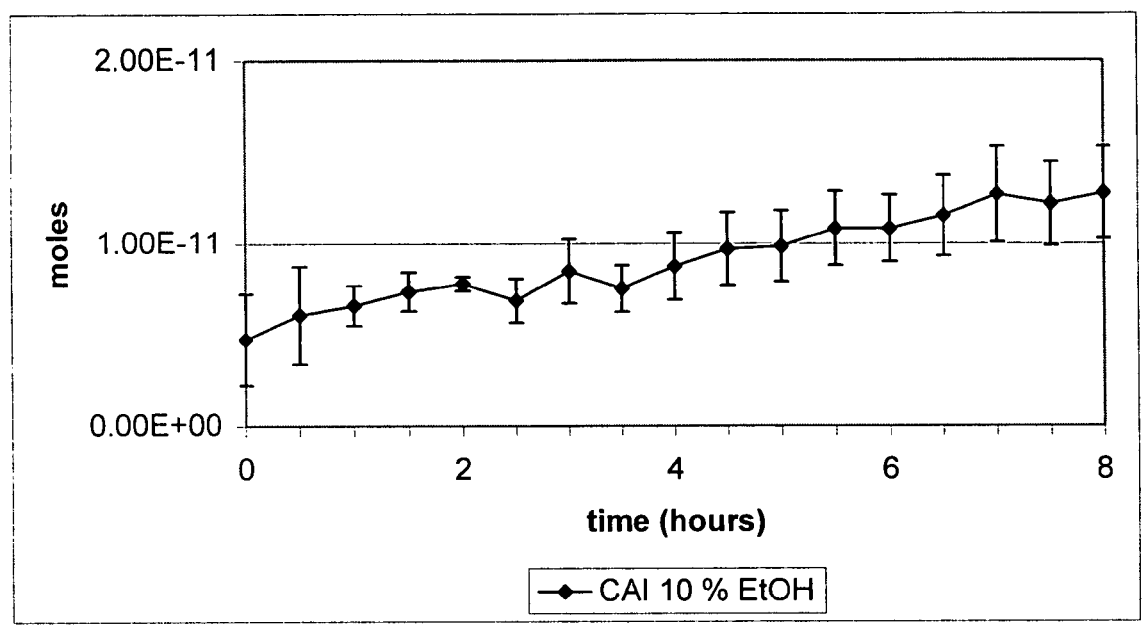
FIG. 6A is a chart illustrating the trans-scleral diffusion of a (mean±SE) 3.3±0.2 µM CAI solution in 10% ethanol (90% BSS) measured over an 8 hour period (n=8). Moles of CAI measured in the receiver chamber as a function of time during BSS perfusion (0.03 ml/min) through the receiver (uveal) chamber. Each point represents the mean±SE.
Figure 6B:
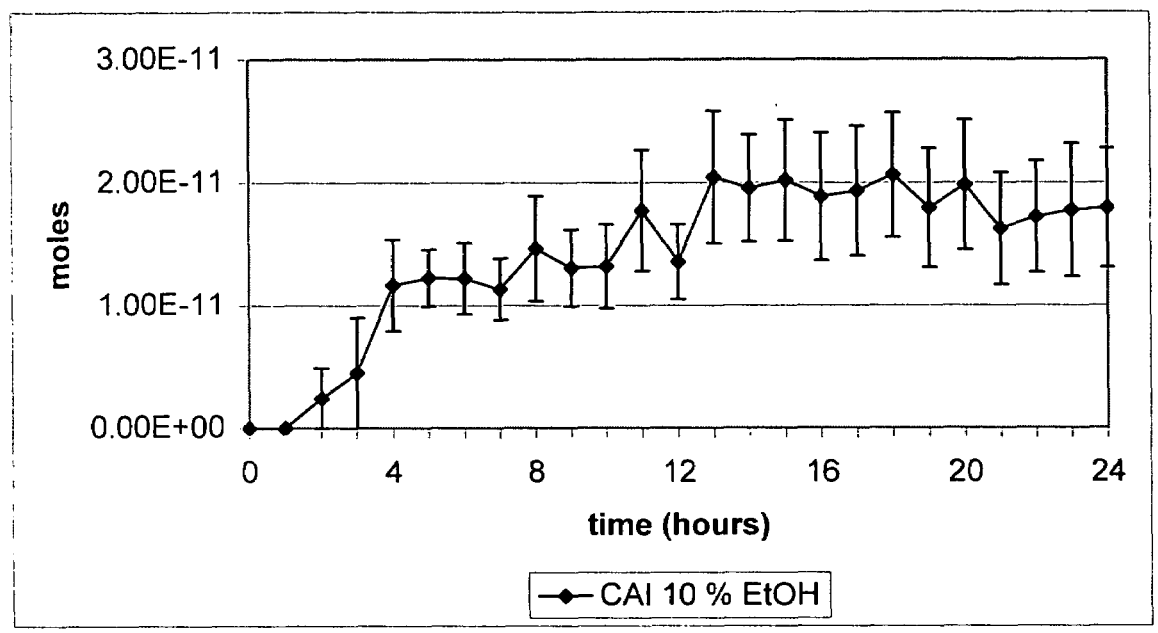
FIG. 6B is a chart illustrating the trans-scleral diffusion of a (mean±SE) 3.3±0.2 µM CAI solution in 10% ethanol (90% BSS) measured over a 24 hour-period (n=4). Moles of CAI measured in the receiver chamber as a function of time during BSS perfusion (0.03 ml/min) through the receiver (uveal) chamber. Each point represents the mean±SE.

FIGS. 3 through 5 show the diffusion through the sclera (in moles) of CAI in the three different solutions over a period of 8 to 24 hours. CAI diffused across the sclera effectively in all three solutions. Solution A (15.2 µM dissolved in 20% DMSO) reached a semi-steady state in approximately 5 hours (FIG. 3), and the permeability constant was measured (mean±SE) at 2.8±0.8×10−6 cm/sec (n=4). The permeability constant for solution B (4.1 µM in 10% DMSO) was measured at 5.5±1.0×10−6 cm/sec (FIG. 4), and steady state was reached in 6 hours (n=7). For solution C (3.3 µM in 10% EtOH) no apparent steady state was observed over the duration of the 8-hour experiment (FIG. 5a, n=8). An additional series of experiments was performed, extending the sampling period to 24 hours. In these experiments a semi-steady state flux was observed at 13 hours (FIG. 5b). The permeability constant was calculated as 4.16±1.1×10−6 cm/sec (n=4). The values, representing semi-steady state permeability for all three solutions appeared comparable, and indeed were not significantly different from each other with ANOVA testing; P value=0.2385.

Transmission electron microscopy (TEM) showed a normal ultrastructure within the sclera for the experiments with CAI in all three test solutions. The sclera shows a densely packed, intramingled arrangement of collagen bundles. There are fibroblasts, longitudinal and transverse collagen lamellae, with variable-diameter fibrils forming the lamellae. The collagen lamellae are more irregularly arranged than observed in the cornea. With all vehicles of DMSO and EtOH in BSS the collagen structure was normal after the 24 hour perfusion experiment.

Other objects, features and advantages of the present invention will be apparent to those skilled in the art. While preferred embodiments of the present invention have been illustrated and described, this has been by way of illustration and the invention should not be limited.

What is claimed is:

1. A method of treating ocular disorders involving angiogenesis, comprising the steps of:
    providing a trans-scleral drug delivery device comprising:
        an insert stabilizer for attachment to a scleral surface and having an interlock opening and an injection port;
        a removable and refillable implant having a reservoir adjacent the scleral surface and an interlock tab, wherein said insert stabilizer and said removable and refillable implant are removeably connectable by mating said interlock tab and said interlock opening and wherein said injection port communicates with said reservoir;
    providing an anti-angiogenic factor;
        introducing said anti-angiogenic factor into said reservoir;
        attaching said insert stabilizer to the scleral surface; and
    refilling said trans-scleral drug delivery device alternately and selectively by
    disengaging said removable and refillable implant from said insert stabilizer, placing a new dosage of angiogenic factor in a pellet form in said reservoir, and re-interlocking said removable and refillable implant with said insert stabilizer, and
    injecting a new dosage of angiogenic factor in liquid form in said reservoir through the injection port.

2. The method of treating ocular disorders as set forth in claim 1, wherein the anti-angiogenic factor is carboxyamido-triazole (CAI).

3. A method of treating ocular disorders involving angiogenesis, comprising the steps of:
    providing a trans-seleral drug delivery device comprising:
        an insert stabilizer for attachment to a scleral surface and having an interlock opening;
        a removable and refillable implant having a reservoir adjacent the scleral surface and an interlock tab;
        interlocking said insert stabilizer and said removable and refillable implant by connecting said interlock tab and said interlock opening;
    providing a pellet of carboxyamido-triazole; and
        placing said pellet in said reservoir;
        attaching said insert stabilizer to the scleral surface; and
    refilling said trans-scleral drug delivery device by disengaging said removable and refillable implant from said insert stabilizer, placing a second pellet of carboxyamido-triazole in said reservoir, and re-interlocking said implant with said insert stabilizer.

* * * * *

UNITED STATES PATENT AND TRADEMARK OFFICE
CERTIFICATE OF CORRECTION

PATENT NO. : 7,276,050 B2
APPLICATION NO. : 10/791487
DATED : October 2, 2007
INVENTOR(S) : Alan Franklin Page 1 of 1

It is certified that error appears in the above-identified patent and that said Letters Patent is hereby corrected as shown below:

| Col. / Line No. | Reads | Should Read |
|---|---|---|
| Col. 8, Line 40 | "providing a trans-seleral" | --providing a trans-scleral-- |

Signed and Sealed this

Twenty-fifth Day of December, 2007

JON W. DUDAS
*Director of the United States Patent and Trademark Office*